US006406484B1

(12) United States Patent
Lang

(10) Patent No.: US 6,406,484 B1
(45) Date of Patent: Jun. 18, 2002

(54) REMOVAL APPARATUS FOR USE IN THE REMOVAL OF IMPACTED CERUMEN FROM THE AUDITORY CANAL

(76) Inventor: Eric L Lang, 6701 Castor Ave., Philadelphia, PA (US) 19149

( * ) Notice: Subject to any disclaimer, the term of this patent is extended or adjusted under 35 U.S.C. 154(b) by 0 days.

(21) Appl. No.: 09/702,635

(22) Filed: Nov. 1, 2000

Related U.S. Application Data

(63) Continuation-in-part of application No. 09/404,696, filed on Sep. 24, 1999, now abandoned.

(51) Int. Cl.[7] ................................................ A61F 11/00
(52) U.S. Cl. ........................................ 606/162; 604/35
(58) Field of Search ................................ 606/162, 109; 604/35, 73, 313, 315, 319, 153, 151, 131

(56) References Cited

U.S. PATENT DOCUMENTS

| | | | |
|---|---|---|---|
| 4,915,691 A | * | 4/1990 | Jones et al. |
| 4,973,311 A | * | 11/1990 | Iwakoshi et al. |
| 5,062,835 A | * | 11/1991 | Maitz et al. ................. 604/153 |
| 5,114,415 A | * | 5/1992 | Shedlock |
| 5,318,548 A | * | 6/1994 | Filshie ......................... 604/35 |
| 6,023,639 A | * | 2/2000 | Hakky et al. ................ 604/313 |
| 6,059,803 A | * | 5/2000 | Spilman ...................... 604/35 |

FOREIGN PATENT DOCUMENTS

WO    WO 90/03194    *   4/1990

* cited by examiner

Primary Examiner—Henry J. Recia
Assistant Examiner—William W. Lewis
(74) Attorney, Agent, or Firm—La Morte & Associates

(57) ABSTRACT

A system and method for removing impacted cerumen from within a person's auditory canal. The system includes a hand held instrument that is held against the ear, and a base that creates a negative pressure in the hand held instrument when it is not in use. The hand held instrument contains an auditory canal plug that seals over the auditory canal when manually biased against the auditory canal. The plug contains an aperture that leads to a vacuum chamber within the hand held instrument. The flow of air through the auditory canal plug and into the vacuum chamber is controlled by a manually operated flow control valve. The hand held instrument merely carries the vacuum chamber. To create a negative pressure in the vacuum chamber, the hand held instrument must be placed on a base. The base contains a vacuum pump that pneumatically interconnects with the vacuum chamber when the hand held instrument is placed on the base. The vacuum pump creates a negative pressure in the vacuum chamber that is maintained in the vacuum chamber even after the hand held instrument is removed from the base.

14 Claims, 3 Drawing Sheets

REMOVAL APPARATUS FOR USE IN THE REMOVAL OF IMPACTED CERUMEN FROM THE AUDITORY CANAL

RELATED APPLICATIONS

This application is a Continuation-In-Part of U.S. patent application Ser. No. 09/404,696, which was filed Sep. 24, 1999, now abandoned.

BACKGROUND OF THE INVENTION

1. Field of the Invention

In general, the present invention relates to devices that are used to remove cerumen from the auditory canal. More particularly, the present invention relates to devices that remove cerumen while creating a negative pressure within the auditory canal.

2. Description of the Prior Art

It is natural for cerumen, i.e. earwax, to collect in the auditory canals. However, with some people, the collection of cerumen becomes troublesome in that it begins to block the auditory canal and adversely affects hearing. It is for these people that cerumen removal products and methods have been developed.

Products to help in the removal of cerumen are produced for use by both doctors and untrained individuals. Products available to individuals typically include a cerumenolytic solution to chemically soften the cerumen and a syringe to flush the softened cerumen from the auditory canal. The flushing of the auditory canal is a relatively safe way for an unskilled person to clean the auditory canal without causing injury to the ear. However, for impacted cerumen, simple flushing techniques are ineffective.

For impacted cerumen, some physical force must be applied to the cerumen to loosen it from the auditory canal. Typically, to apply the physical force needed, some type of instrument is entered in to the auditory canal. The instrument is used to contact the cerumen and dislodge the cerumen from the auditory canal. Such prior art instruments are exemplified by U.S. Pat. No. 5,888,199 to Karell, entitled Ear Cleaning Device With A Flexion Part; U.S. Pat. No. 5,374,276 to Lay, entitled Ear Wax Remover; and U.S. Pat. No. 5,715,850 to Markgraaf, entitled Personal Ear Cleaning Device. Instruments that enter the auditory canal have the potential of causing severe injury to the ear if not handled properly. Accordingly, instruments that enter the auditory canal are not typically sold to the public, but are, rather used by physicians. However, even when used by physicians, instruments that enter the auditory canal have the inherent potential of contacting the eardrum and causing injury.

U.S. Pat. No. 6,059,803 to Spilman, entitled Ear Vacuum, discloses an instrument that uses air pressure, rather than mechanical probe, to dislodge ear wax. The instrument is a battery operated device that reduces the air pressure in the auditory canal in an attempt to suction the cerumen out of the auditory canal. A problem associated with such instruments is that the weight of the vacuum motor and the batteries make the device difficult to manipulate and hold in place outside a patient's ear. Furthermore, cerumen is a highly viscous material. The degree of vacuum needed to separate cerumen from the tissue of the auditory canal and suction the cerumen completely out of the auditory canal is significant. This needed degree of suction often cannot be achieved within the auditory canal without causing harm to the tympanic membrane and/or severe discomfort to the patient.

A need therefore exists for a device and method that can apply a physical force to impact cerumen in the auditory canal with air pressure. This need met by the present invention as is described and claimed below.

SUMMARY OF THE INVENTION

The present invention is a system and method for removing impacted cerumen from within a person's auditory canal. The system includes a hand held instrument that is held against the ear, and a base that creates a negative pressure in the hand held instrument when it is not in use. The hand held instrument contains an auditory canal plug that seals over the auditory canal when manually biased against the auditory canal. The plug contains an aperture that leads to a vacuum chamber within the hand held instrument. The flow of air through the auditory canal plug and into the vacuum chamber is controlled by a manually operated flow control valve.

The hand held instrument merely carries the vacuum chamber. To create a negative pressure in the vacuum chamber, the hand held instrument must be placed on a base. The base contains a vacuum pump that pneumatically interconnects with the vacuum chamber when the hand held instrument is placed on the base. The vacuum pump creates a negative pressure in the vacuum chamber that is maintained in the vacuum chamber even after the hand held instrument is removed from the base. The vacuum chamber is used to create a controlled degree of suction that is used to create a controlled degree of suction that is used to loosen the cerumen and cause it to migrate to a readily accessible location within the auditory canal.

BRIEF DESCRIPTION OF THE DRAWINGS

For a better understanding of the present invention, reference is made tot he following description of exemplary embodiments thereof, considered in conjunction with the accompanying drawings, in which.

DETAILED DESCRIPTION OF THE INVENTION

The present invention is a lightweight instrument that uses air pressure to loosen cerumen that is impacted within the auditory canal. The instrument does not attempt to suction the cerumen completely out of the auditory canal. Rather, the instrument gently loosens the impacted cerumen and draws the loosened cerumen toward the end of the auditory canal nearest the pinna. Once at this location, the loosened cerumen can be physically removed with a swab or similar implement.

Figure 1:
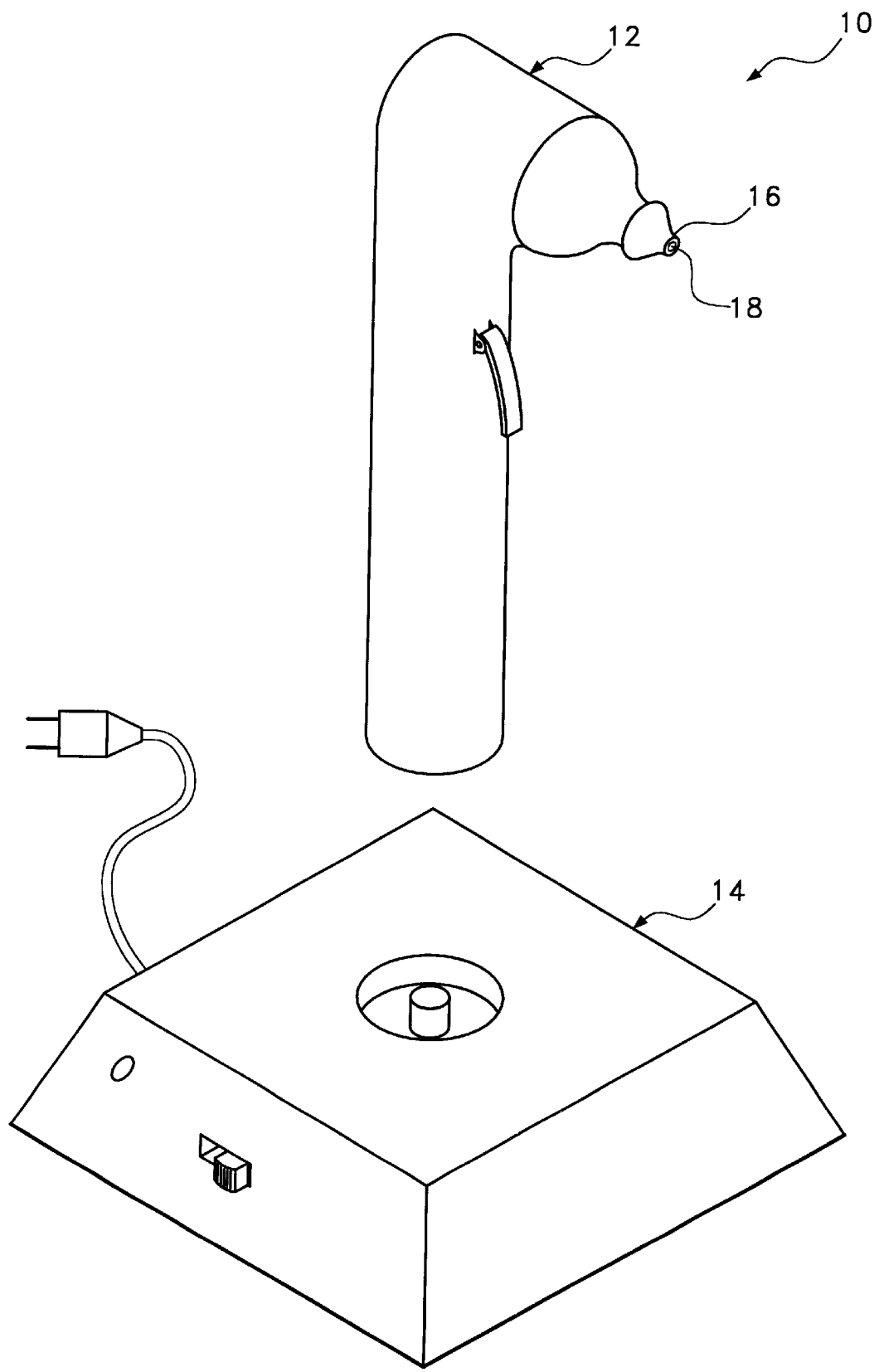
FIG. 1 is a perspective view of an exemplary embodiment of the present invention device.

Referring to FIG. 1 an exemplary embodiment of a cerumen removal system 10 is shown in accordance with the present invention. The cerumen removal system 10 consists of a hand held instrument 12 and a base 14 that supports the hand held instrument 12. The hand held instrument 12 contains an elastomeric plug 16 that is inserted into the open end of the auditory canal. An aperture 18 extends through the elastomeric plug 16. A negative pressure is created within the aperture 18. As will be explained, the negative pressure is used to loosen any cerumen impacted within the auditory canal and causes that cerumen to migrate towards the open end of the auditory canal.

Figure 2:
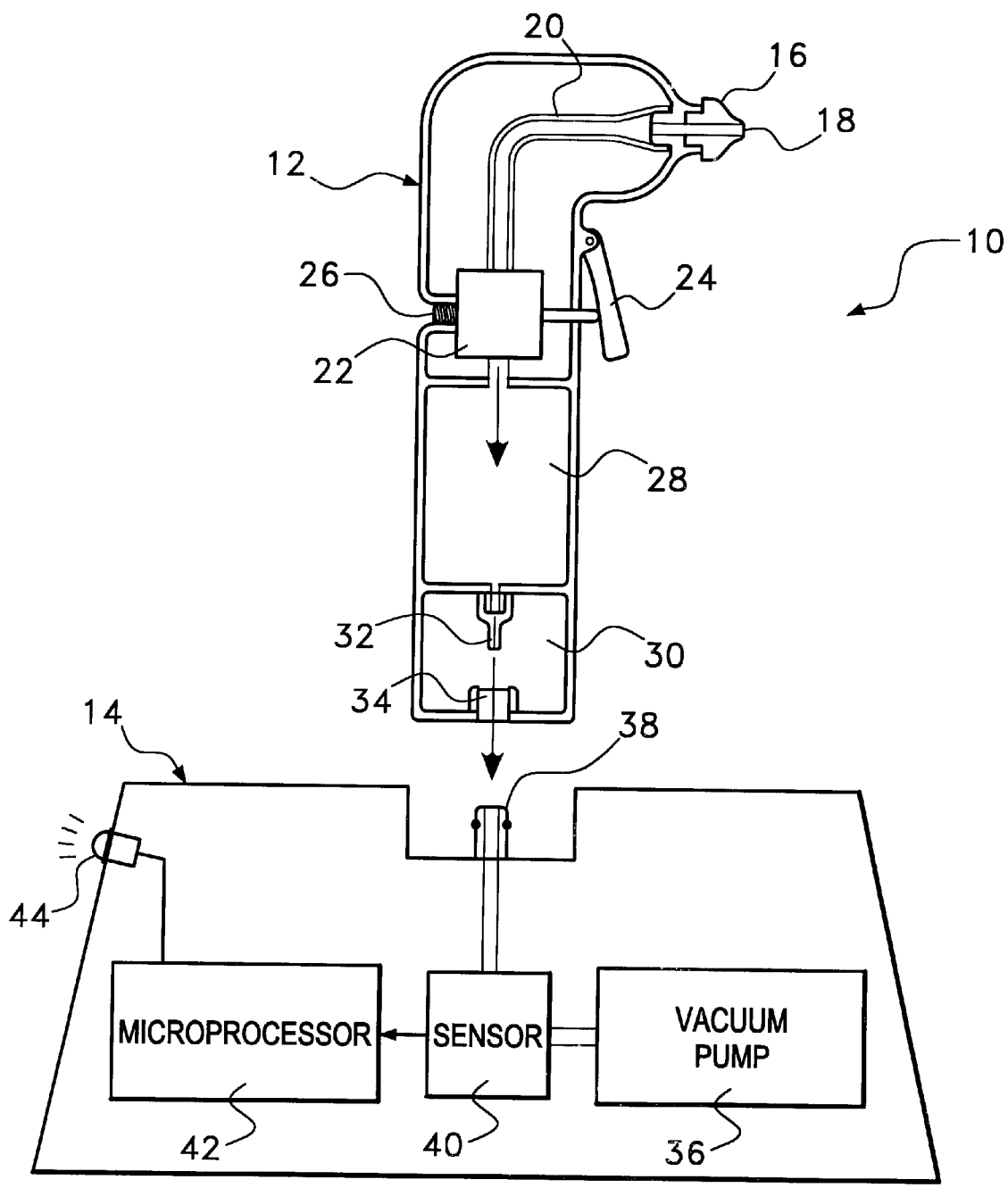
FIG. 2 is a schematic view of the embodiment shown in FIG. 1.

Referring FIG. 2, it can be seen that the aperture 18 that leads through the elastomeric plug 16 leads into a tube 20. The tube 20 leads to a flow control valve 22. The flow control valve 22 has adjustable controls. The first control is a trigger control 24 that is used to selectively open and close the flow control valve 22. The trigger control 24 is manually operated by the physician holding the instrument 12. The second control is an adjustment screw 26. The adjustment screw 26 control valve 22 when the flow control valve 22 is open. As such, the trigger control 24 opens and closes the flow control valve 22 and adjustment screw 26 adjusts the flow rate through the flow control valve 22 when it is open.

The flow control valve 22 controls the flow of air between the aperture 18 in the elastomeric plug 16 and a primary vacuum chamber 28. the primary vacuum chamber 28 has a volume of several cubic centimeters. The pressure within the primary vacuum chamber 28 is held below ambient. As such, when the flow control valve 22 is opened, suction is created at the aperture 18 in the elastomeric plug 16.

The primary vacuum chamber 28 is coupled to a secondary vacuum chamber 30 with a one way valve 32. At the bottom of the secondary vacuum chamber 30 is an open coupling 34. In the shown embodiment, the hand held instrument 12 does not contain a vacuum pump needed to reduce pressure in the primary vacuum chamber 28. A vacuum pump 36 is located in the base 14 of the cerumen removal system 10. As is shown in FIG. 2, a vacuum pump 36 is connected to a pneumatic nipple 38 within the base 14. As the hand held instrument 12 is placed on the base 14, the pneumatic nipple 38 interconnects with the open coupling 34 at the bottom of the secondary vacuum chamber 30. The vacuum pump 36 within the base 14 can be controlled by an electric on/off switch. The on/off switch can be either located on the exterior of the base 14, or can be located next ti the pneumatic nipple 38. If placed next to the pneumatic nipple 38, the on/off switch can be activated by the placement of the instrument 12 onto the base 14.

Once the instrument 12 is connected to the base 14 and the vacuum pump 36 is activated, the vacuum pump 36 lowers the air pressure within the secondary vacuum chamber 30. As a pressure differential develops between the secondary vacuum chamber 30 and the primary vacuum chamber 28, the one way value 32 opens and air is evacuated from the primary vacuum chamber 30 and the primary vacuum chamber 28 meet the suction rating of the vacuum pump 36, the hand held instrument is ready for use.

In an alternate embodiment, a pressure sensor 40 can be located in the base 14, wherein the pressure sensor 40 measures the pressure created by the vacuum pump 36 in the secondary vacuum chamber 30. The pressure sensor 40 is connected to a microprocessor 42 that controls the vacuum pump 36. Once a predetermined pressure is created in the secondary vacuum chamber 30, the microprocessor 42 stops the vacuum pump 36. An indicator light 44 can be used to provide a visual indication of when a proper operating pressure has been obtained in the hand held instrument 12.

To use the hand held instrument 12, the hand held instrument 12 is placed on the base 14 and the primary vacuum chamber 28 and secondary vacuum chamber 30 are both depressurized. Once the vacuum chamber 28, 30 are at the desired negative pressure, the hand held instrument 12 is removed from the base 14. Once removed from the base 14, the secondary vacuum chamber 30 vents to ambient pressure through the open coupling 34. However, due to the presence of the one way valve 32, the primary vacuum chamber 28 remains at the desired negative pressure.

Figure 3:
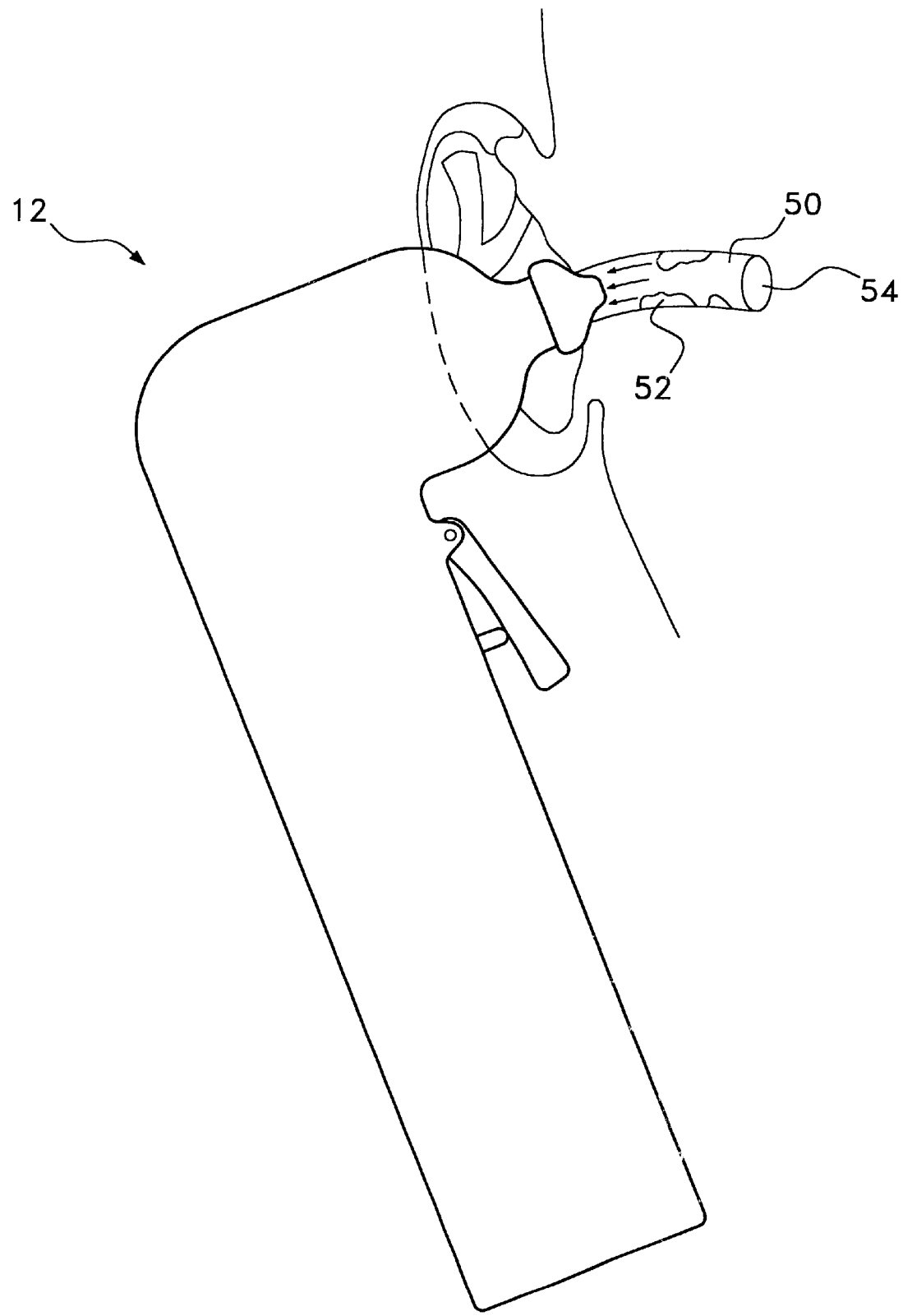
FIG. 3 is a fragmented view of the embodiment shown in FIG. 1, shown in conjunction with a cross section of the auditory canal.

Referring to FIG. 3, an auditory canal 50 is shown containing sections of impacted cerumen 52 that need to be removed. At the end of the auditory canal 50 is the tympanic membrane 54. It is the tympanic membrane 54 that becomes damaged should it be contacted by an ear cleaning instrument. If the tympanic membrane 54 is contacted and ruptured, a person has the injury commonly referred to as a broken ear drum.

The hand held instrument 12 is used to loosen impacted cerumen 52 in the auditory canal 54 using air pressure. From FIG. 3, it can be seen that the hand held instrument 12 is placed against the ear. The elastomeric plug 16 is made of a soft elastomeric material and seals against the open end of the auditory canal 50 when placed in the ear. The seal made between the auditory canal 50 and the elastomeric plug 16 is air tight provided the elastomeric plug 16 is manually biased against the auditory canal 50 with sufficient force.

To activate the hand held instrument 12, the trigger control 24 (FIG. 2) connected to the flow control valve 22 (FIG. 2) is depressed. This evacuates air from the tube 20 (FIG. 2) leading to the elastomeric plug 16. The lower air pressure in the tube causes the air to be drawn into the aperture 18 of the elastomeric plug 16. The change in air pressure is transferred to the auditory canal 50 where the negative air pressure acts to dislodge the impacted cerumen 52 without physically contacting the cerumen 52 or damaging the tympanic membrane 54.

Prior to the use of the hand held instrument 12, the auditory canal 50 is treated with a cerumenolytic solution to soften the impacted cerumen 52. As the air pressure within the auditory canal 50 is lowered by the hand held instrument 12, the loosened cerumen 52 is drawn toward the open end of the auditory canal 50. As the softened cerumen 52 migrates within the auditory canal 50, it displaces other areas of cerumen 52 that may not have been otherwise effected by the cerumenolytic. solution and changing air pressure.

The suction provided by the hand held instrument 12 draws the cerumen 52 towards the open end of the auditory canal 50. However, the cerumen 52 is highly viscous. The volume of suction provided by the hand held instrument 12 is insufficient to lift the cerumen 52 out of the auditory canal 50. Rather, the volume of suction is sufficient enough only to dislodge the impacted cerumen 52 and cause migration in the cerumen 52. If the volume of suction were sufficient enough to suck up the cerumen 52, damage to the tympanic membrane could easily occur. Consequently, the level of suction is controlled to a point where it merely causes migration of the cerumen 52 in the auditory canal 50.

Once the cerumen 52 is drawn away from the tympanic membrane 54, the cerumen 52 becomes visible in the auditory canal 50 as it approaches the open end of the auditory canal 50. At this point, a physician can physically remove the cerumen 52 using a swab or similar instrument.

It will be understood that the specifics of the present invention described above illustrated only an exemplary embodiment of the present invention. A person skilled in the art can therefore make numerous alterations and modifications to the shown embodiment utilizing functionally equivalent components to those shown and described. All such modification are intended to be included within the scope of the present invention as defined by the appended claims.

What is claimed is:

1. A system for removing cerumen from the auditory canal, comprising:
   a hand held assembly including:
      an auditory canal plug defining a central aperture, wherein said auditory canal plug covers the auditory canal and said central aperture communicates with the ear canal when manually biased against the auditory canal;
      a primary vacuum chamber having an inlet and an outlet;
      a one-way valve in said primary vacuum chamber for providing a one way flow of air from said primary vacuum chamber through said outlet;
      a flow control valve coupled between said auditory canal plug and said inlet of said primary vacuum chamber for selectively controlling the flow of air into said primary vacuum chamber from said central aperture;
   a base assembly containing a vacuum pump, said base assembly being selectively interconnectable with said outlet of said hand held assembly, wherein said vacuum pump creates a predetermined pressure in said primary vacuum chamber when said hand held assembly and said base assembly are interconnected.

2. The system according to claim 1, wherein said hand held assembly further includes a secondary vacuum chamber coupled to said primary vacuum chamber, wherein said primary vacuum chamber and said secondary vacuum chamber are interconnected by said one way valve that only permits air flow from said primary vacuum chamber into said secondary vacuum chamber.

3. The system according to claim 2, wherein said base assembly contains a coupling that leads to said vacuum pump, wherein said coupling engages said secondary vacuum chamber in said hand held assembly when said hand held assembly is connected to said base assembly, and creates said predetermined pressure in said secondary vacuum pressure.

4. The system according to claim 1, wherein said flow control valve includes a manual control for manually opening and closing said flow control valve.

5. The system according to claim 4, wherein said flow control valve has a flow rate when open, and said flow control valve includes an adjustment mechanism for adjusting said flow rate.

6. A system for removing cerumen from the auditory canal, comprising:
   an instrument assembly containing an internal vacuum chamber, an auditory canal plug coupled to the internal vacuum chamber and a flow control valve disposed between the internal vacuum chamber and the auditory canal plug to regulate the flow of air into the vacuum chamber through the auditory canal plug, said internal vacuum chamber having an outlet with a one-way valve for preventing flow of air into said internal vacuum chamber through said outlet;
   a base assembly for selectively holding said instrument assembly when said instrument assembly is not in use, said base assembly containing a vacuum source selectively interconnected to said vacuum chamber for evacuating said vacuum chamber in said instrument assembly when said instrument assembly is held by said base.

7. The system according to claim 6, wherein said instrument has an external lever control that controls said control valve.

8. The system according to claim 6, wherein said hand held assembly further includes a second vacuum chamber coupled to said outlet of said vacuum chamber, wherein said internal vacuum chamber and said second vacuum chamber are interconnected by said one way valve that only permits air flow from said internal vacuum chamber into said second vacuum chamber.

9. The system according to claim 8, wherein said base assembly contains a coupling that leads to said vacuum source, wherein said coupling engages said second vacuum chamber in said instrument assembly when said instrument assembly is connected to said base assembly and evacuates said second vacuum chamber within said internal vacuum chamber.

10. The system according to claim 6, wherein said flow control valve includes a manual control for manually opening and closing said flow control valve.

11. The system according to claim 10, wherein said flow control valve has a flow rate when open, and said flow control valve includes an adjustment mechanism for adjusting said flow rate.

12. A method of removing cerumen from the auditory canal, comprising the steps of:
    softening cerumen in the auditory canal with a solution;
    providing an instrument having an auditory canal plug, an internal chamber, an evacuation port for evacuating air from said internal chamber and a one-way valve that prevents air flow from flowing into said internal chamber through said evacuation port;
    providing a vacuum source separate from said instrument, wherein said instrument can be selectively interconnected with said vacuum source;
    evacuating said internal chamber in said instrument by selectively connecting said evacuation port of said internal chamber to said vacuum source;
    covering the auditory canal with said auditory canal plug;
    interconnecting said internal chamber to said auditory canal plug, wherein said internal chamber draws air from the auditory canal through the auditory canal plug and creates a negative pressure within the auditory canal, wherein said negative pressure is sufficient to cause migration of the cerumen within the auditory canal; and
    physically removing the cerumen from the auditory canal once the cerumen becomes accessible within the auditory canal.

13. The method according to claim 12, wherein said step of softening cerumen in the auditory canal includes introducing a cerumenolytic solution into the auditory canal.

14. The method according to claim 12, wherein said sub-step of interconnecting said internal chamber to said auditory canal plug includes manually opening a flow control valve disposed between said internal chamber and said auditory canal plug.

* * * * *